United States Patent [19]

Thoma et al.

[11] Patent Number: 4,781,688
[45] Date of Patent: Nov. 1, 1988

[54] DISPENSING DEVICE FOR A LIQUID MEDICAMENT

[75] Inventors: Herwig Thoma, Wiesengasse 3, A-1140 Wien; Michael Krötlinger, Traisen, both of Austria

[73] Assignee: Herwig Thoma, Vienna, Austria

[21] Appl. No.: 34,884

[22] Filed: Apr. 6, 1987

[30] Foreign Application Priority Data

Apr. 4, 1986 [AT] Austria .................................. 891/86

[51] Int. Cl.⁴ .............................................. A61M 5/00
[52] U.S. Cl. .................................. 604/132; 604/134; 128/DIG. 12
[58] Field of Search ............... 604/132, 134, 136, 890, 604/891, 65; 128/DIG. 12; 222/95, 103

[56] References Cited

U.S. PATENT DOCUMENTS

| | | |
|---|---|---|
| 3,604,417 | 9/1971 | Stolzenberg et al. . |
| 3,698,595 | 10/1972 | Gortz et al. ...................... 604/132.2 |
| 4,209,014 | 6/1980 | Sefton . |
| 4,265,241 | 5/1981 | Portner et al. . |
| 4,360,019 | 11/1982 | Portner et al. . |
| 4,505,710 | 3/1985 | Collins . |
| 4,557,728 | 12/1985 | Sealfon et al. ...................... 604/134 |

FOREIGN PATENT DOCUMENTS

| | | |
|---|---|---|
| 360636 | 1/1981 | Austria . |
| 378123 | 6/1985 | Austria . |
| 0019814 | 12/1980 | European Pat. Off. . |
| 0091624 | 10/1983 | European Pat. Off. . |
| 0098893 | 1/1984 | European Pat. Off. . |
| 0128703 | 12/1984 | European Pat. Off. . |
| 2124062 | 8/1979 | Fed. Rep. of Germany . |
| 2201533 | 9/1980 | Fed. Rep. of Germany . |
| WO85/02344 | 6/1985 | World Int. Prop. O. . |

OTHER PUBLICATIONS

IEEE Transactions on Biomedical Engineering, vol. BME 28, No. 3, Mar. 1981, A Review of Programmed Insulin Delivery Systems, W. J. Spencer, Fellow IEEE, pp. 237-251.

Primary Examiner—Stephen C. Pellegrino
Attorney, Agent, or Firm—Herbert Dubno

[57] ABSTRACT

A dispensing device for a liquid medicament has a cylindrical support formed on a base which receives an application part fitted into this support and costituting a projection from a cover. An annular reservoir braced against the support is pressed inwardly by a prestressed annular body which can be formed integrally with the reservoir of silicone rubber to drive a liquid medicament through the passage formed in the application part into the body at a constant rate.

19 Claims, 3 Drawing Sheets

4,781,688

DISPENSING DEVICE FOR A LIQUID MEDICAMENT

FIELD OF THE INVENTION

Our present invention relates to a device for dispensing a liquid medicament and, more particularly, to a device for administering a liquid medicament to a patient at a constant rate.

BACKGROUND OF THE INVENTION

While devices for administering liquid medicaments to patients have been provided heretofore in a variety of forms, this invention provides a device for the purpose of the type which comprises a housing, a compressible flexible reservoir for receiving the medicament in this housing, a filling valve to enable filling of the reservoir, a passage communicating with the reservoir and of a defined cross section and length so as, at least in part, to control the rate of outflow to the patient and, connected with this passage, a suitable outlet cannula designed to suit the particular application, e.g. a catheter or a needle.

Such devices can also be termed infusion pumps and infusion pumps are utilized in the treatment of patients in a limited number of cases for particular disorders. There are two basic fields of application of such infusion pumps:

In one field, a pharmacological substance can be used to treat a local disorder of a particular organ (e.g. pain). In a second field of application, the infusion pump can be utilized to improve a bodily function which is insufficient (e.g. blood purification) or can be employed to relieve an acute crisis condition.

An example of the latter application is the infusion of an antiarrhythmic pharmaceutical for patients of cardiac disorders resulting from variation in pacemaker activity. Such devices serve primarily to prevent heart failure because the timing of the infusion prevents or interrupts an arrhythmic condition. Such pumps are usually implanted.

Another group of pumps represent the types utilized to replace an insufficiency of certain body fluids of particular organs and which lack represent a pathological condition itself. The replacement of such body fluids falls in the realm of endocrinology.

A particular example in which the failure of an organ can result in a deficiency of supply of a particular liquid requiring the infusion of a substitute, is the failure of the pancreas to produce sufficient insulin, a body fluid which is essential to life.

At the present time, patients suffering from an insulin deficiency are treated mainly by injection of insulin, a therapy which, after several years, can give rise to various organ failures.

A further group of patients may require blood replacement therapy or synthetic blood cleaning.

In many modes of treatment heretofore employed, the fluid required for body treatment hereinafter referred to a a liquid medicament whether it is a replacement fluid, a fluid utilized to provide a blood cleaning or like function of a pharmaceutical used for treatment or relief of a particular symptom, is provided in a storage receptacle and delivered to the body of the patient by a pump unit, the storage receptacle being refilled at intervals.

The application can be oral (resorption of the liquid via the intestinal tract), subcutaneous (resorption via the lymph system) or venous or arterial, i.e. intravenous or intraarterial. Intraperitoneal infusions are today used in treatment only for insulin therapy.

While the present invention has a principal application in the subcutaneous infusion of insulin and may be described hereinafter in this connection, it will be understood that in principle it can be used wherever a constant-rate therapy with an infusion pump from which the liquid medicament is delivered to an organ of the body at a substantially constant flow rate, can be utilized for various purposes including:

(1) to cover the basal requirement, especially when, as is often the case, long action duration insulin is effective;

(2) where peripheral insulin resistance requires application of the normal insulin requirement uniformly over the entire day for a positive therapeutic effect; and (3) where the treatment is of the so-called type II disorder, where the infusion of insulin is required to cover the prandial (food intake) requirements to permit the pancreas to have a rest function which enables its recovery and thus makes the pancreas better able to perform the normal sensor function and normal insulin supply.

However, it should be understood, as to the invention, that it is in no way limited to the subcutaneous application of insulin. Indeed, it is useful wherever long term injection of a liquid is required or desirable, e.g. for the exact dosing of medicaments for blood purification, for local treatment with antibiotics and for local analgesic therapy. Since the device of the invention can also be implanted, it can eliminate drawbacks of a host of the prior art implanted infusion pumps.

In order to appreciate the various problems which are solved by the device of the invention, it is important to understand some of the requirements for both insulin pumps which are applied on the surface of the body and those which are implanted. Infusion systems which normally mounted on the bed of a patient need not be discussed since they are far more remote from the invention.

The following list defines the biological and technical categories of problems:

(a) life of the pump, e.g. the length of time the pump remains operative without requiring replacement;

(b) reliability and redundancy;

(c) controllability of the pump and the manner (power source) by which it is driven;

(d) biological sensor for automatic control (closed loop) of the infusion;

(e) durability and function of the output cannula;

(f) energy supply; and (g) safety.

Other criteria such as implantability and price, also play a role.

In practice, the implantation pumps provided at the present time for a constant delivery rate can comprise a flexible insulation container at a superatmospheric pressure with the flow controlled by a throttle or a cross-section-reducing cannula. These all deliver insulin at a rate which is proportional to pressure.

The pressure is supplied, generally with the aid of an intervening membrane by a drive gas (FREON). A drive gas can be used as the energy source for a pump in the manner described, for example, in Europatent publication EP-OS 0128703 for delivering the liquid via a valve which can be controlled by the patient and is external of the patient body.

An interesting concept, which is nevertheless affected with all of the problems of high energy requirements, is found in U.S. Pat. No. 4,505,710 in which the control of a piston is effected by two reciprocal chambers supplied with the drive gas. The piston is shifted by heating the chambers on respective sides thereof electrically so that the higher vapor pressure on the respective side shifts the piston. In this system, the flow throttle is eliminated.

The latter also applies to the system described in Europatent publication EP-OS No. 0091624 which utilizes vapor pressure as an energy source. Here, the vapor transits through a semipermeable membrane which delays passage of the gas.

A superatmospheric pressure also operates the pump described in Europatent publication EP-OS No. 0098893 in the construction between a high pressure gas chamber and the medicament receptacle to a further closed compartment is prevented. A fine control valve of the gas container supplies the intermediate compartment with pressure which then operates upon the flexible medicament.

Other known pump systems (German printed application DE-AS No. 2124062 and U.S. Pat. No. 38,356) deal with further developments of transportational systems.

For example, the Siemens firm of West Germany has developed a miniaturized roller-type peristaltic pump which can be carried easily on the body and controlled by the patient.

An implantable control has also been developed as will be apparent from German Open Application DE-OS No. 3,018,833 and the Europatent application No. 0019814. The function of such implantable dispensers is theoretically advantageous, since it allows the patient to eat at will, but the implantation itself is fraught with difficulty.

For example, the quantity of the liquid infused into the body is dependent upon the elasticity of a silicone rubber tube and it has long been recognized that silicone rubber in the body especially in direct contact with the body tissues, will degenerate. In practice, it has been found that the useful life of such pumps will be from one to a maximum of two years. The pumps are driven by small stepping motors with transmissions and these elements also have a limited reliability in biological milieus. A highly stable system is described in the International application WO-OS No. 8502344. Here a flexible liquid receptacle (i.e. a metal bellows) is compressed by a device which in principal includes a spindle driven by an electric motor. Osmotic forces are also used to compress the elastic medicament receptacle.

Thus, for example, in the German printed application No. 2,201,533 (based upon a U.S. Patent application Ser. No. 106,161) describes various designs involving two flexible receptacles of which a first (medicament receptacle) is compressed by the second osmotically active receptacle.

A common characteristic of the various designs is a rigid outer housing so that the water uptake by the osmotically active material will result in an enlargement of the osmotic receptacle which is thereby confined so that its pressure can be applied to the medicament receptacle.

Among the various designs is a torus-like configuration. However, it can be remarked that the physical principle by which these designs of infusion pumps operate is significantly different from the physical principle under which the invention operates.

An improvement utilizing the osmotic principle is described in U.S. Pat. No. 3,604,417. In this system, the medicament part of the device is separated from the osmotic drive and the latter comprises two shiftable pistons having a defined range of action for the osmotic material.

A further known pump system operates in the form of a membrane pump with intake and discharge valves. Such pumps have long useful lives, but have problems with respect to their size, since liquid controlled valves generally are sizeable because they require a valve seat, a valve member engageable with the seat, a restoring spring acting on the valve member . . . . Another important disadvantage of such valves is their opening and closing characteristics.

If one wishes to pump 1 to 2 $\mu$l and for closing a valve several $\mu$l is required, this can create a problem. Indeed, when the pump is to deliver a volume with precision and deviations of say 50% (amounting to 1 $\mu$l) may result, as in such cases, the pump may be unsatisfactory.

U.S. Pat. Nos. 4,265,241 and 4,260,019 describe similar pumps, the latter representing a further development of a same basal construction.

In this latter pump configuration, the safety aspect has been considered and valve redundancy has been introduced together with a special device for generating a reduced pressure in the liquid receptacle so that upon failure of the valve system there will be no direct danger for the patient.

Because of dimensional considerations with such dispensers, however, there is a limitation on the size of the liquid receptacle which can only work with low-concentration insulin so that a high refilling rate (for example, every two weeks) results. This is not acceptable for most patients.

In U.S. Pat. No. 4,209,014, there is described a system involving a mechanical pressing of an elastic but permeable synthetic resin with the aid of an electromagnetically driven piston. The synthetic resin which does not have a closed structure, for example foam rubber or polyurethane foam, is slightly permeable to pharmaceuticals. If such a synthetic resin is mechanically compressed with the aid of a piston, the flow rate can be significantly increased.

The advantage of simplified construction, however, is associated with disadvantages, for example the compression can increase the quantity delivered only by a factor of three. The throughflow in the noncompressed rate of the synthetic resin requires nonetheless a primary pressure in the liquid vessel. A long operating life cannot be ensured for such purposes, since the long term elasticity of the synthetic resin which is required for an exact metering of material, cannot be ensured. Furthermore, the energy consumption in compression of such elastic materials is relatively large in the device of this patent (greater than 1 watt).

In Austrian Patent No. 378,123, a special configuration of two pistons and two cylinders composed of metal is described. This system has the advantage of long operating life. The device operates by the drawing principal and does not require any conventional valves with valve springs. The features of this construction include the low drawing volume (0.3 to 1.5 $\mu$l per cycle), a pump volume determined by the number of pump cycles, and electromagnetic control of the pump.

Finally, mention must be made of the Austrian Pat. No. 360,636 which describes a dispenser and can be said to form the starting point for the present invention. In this case, a sausage-shaped tube of a special synthetic resin material is inflated, because of its special construction with a liquid so that upon emptying, over a predetermined range of elasticity, it is possible to generate a substantially constant pressure versus time characteristic (the term "constant" here permitting in accordance with the teachings of the Patentee a fluctuation of about 10%).

The system of this latter patent has a number of disadvantages including the retention of a high residual volume in the tube following the discharge over the constant rate portion. The design also is intended exclusively for external use. Only a limited number of synthetic materials can be used, since only such materials have the required characteristics. It is also questionable whether the materials used are biocompatible and compatible with the liquids to be dispensed, since many of the medicaments, such as insulin, are highly sensitive.

Since the system is not prestressed and only the linear region of the force dilation curve is usable, there is a further loss in volume deliverable at a constant rate.

Externally driven pumps utilizing the same principles or implantable pumps (piston pumps, roller peristaltic pumps . . . ) are utilized in miniaturized mechanical or spindle-driven form and includes spindle drives for hypodermic syringes and the like. Such pumps can have speed controls. The state of the art also has developed programs for control, for example, a precalculated daily profile for insulin delivery (See W. J. SPENCER, *A Review of Programmed Insulin Delivery Systems: IEEE Transactions on Biomedical Engineering*, Vol. BME-28 No. 3, March 1981).

Drawbacks and discomforts resulting from such external pumps include:

(a) excessive bulk of the entire pump system and marginal acceptability of them by patients on social grounds;

(b) excessive service costs, especially for programmable pumps which are fraught with optional failures and can introduce the risk of hypoglycemia for the patient;

(c) problems of hygiene in carrying the pumps (e.g. in showering or bathing);

(d) unsatisfactory condition relating to the outlet in cannula, e.g. in the case of injection, needles, an inflammation resulting from long term lying, sensitivity and also, for example dislocation upon tension applied to the catheter;

(e) high price: generally ranging between 30,000 to 50,000 Austrian Schilling corresponding to approximately $2,500.-to $4,000.-.

The following disadvantages characterize gas-driven pumps:

(a) variation of the delivered dose resulting from temperature fluctuations, e.g. in the case of a feverish patient;

(b) a reduced absolute pressure of the drive gas and a consequent alteration in pump volume in dependence upon sea level, causing problems with respect to patients who are flying or in sea travel;

(c) the need for a metal bellows because of detrimental effects of the drive gases;

(d) variation in the pump rate of up to 50% upon emptying of the pump resulting from the intrinsic characteristics of the metal bellows required to separate the liquid and the drive gas.

OBJECTS OF THE INVENTION

It is, therefore, the principal object of the present invention to provide an improved pump for the dispensing of a liquid medicament at a substantially constant rate which will avoid the drawbacks enumerated above.

Another object of this invention is to provide an infusion pump which fulfills the following quality criteria of a basal rate pump:

(a) simple construction;

(b) minimum volume and weight;

(c) low fabrication cost associated with the possibility that the pump may be a disposable or single-use article;

(d) reduced service cost;

(e) high reliability so that it can be used effectively even with aged and infirmed patients;

(f) small or negligible residual medicament volume;

(g) it is composed of an insulated compatible material; and (h) function with precision over the entire range of emptying.

SUMMARY OF THE INVENTION

These objects and others which will become apparent hereinafter are attained, in accordance with the invention, with a device for administering a liquid medicament to a patient at a substantially constant rate which comprises a cylindrical support formed on a lower portion or base of a housing and around which a flexible reservoir for the liquid medicament extends in a ring, and a radially elastically prestressed annular body surrounding the reservoir and bearing thereon for the constant-pressure compression of the liquid medicament in the reservoir, the prestress preceding filling of the reservoir with the liquid.

With this construction, the invention satisfies all of the above-listed criteria and one of the main differences between the invention and earlier proposals resides in the special geometry for generating a constant pressure over the entire emptying process or duration.

A constant flow rate or discharge rate is considered to be achieved when the pressure on the liquid in the reservoir remains constant during the entire emptying process.

The invention has as its underlying motivation a physical relationship which is developed below:

The pressure is basically defined as a quotient, namely force per unit area. The pressure of a given device is determined, therefore, by the force which acts upon a given surface. It is unavoidable that the geometry of a reservoir which is collapsible will change as the reservoir is emptied. A constant pressure under these conditions can thus be achieved over the entire emptying interval or perimeter when:

(1) The change in the surface area of the reservoir with its reduction in volume during the expression of the liquid ($\Delta A$) is proportional to the reduction of the compressing force ($\Delta F$) during this process;

(2) There is a linear relationship between force and surface area; and (3) It is possible to modify the characteristic of the elastic ring so as to provide such a relationship.

In the system of the invention, during the emptying of the pump reservoir and its reduction in volume, the periphery of a cylinder ring is proportionally reduced. This ring can be a cylindrical wall of the reservoir which is driven inwardly by contraction of the elastic body.

The reduction of the periphery which is also proportional to the reduction of the radius, results, in light of the spring characteristic of the annular body, in a proportional relieving of the spring element and thus a proportional reduction in the force applied.

For a cylinder of a fixed height, the pressure is replaced by the quotient between force and surface area which in simple terms can be represented by the surface area of the cylindrical wall which is pressed inwardly by the annular elastic body. The pressure is then constant when there is a proportionality between the distension of this wall and the force. According to the invention, the linear dependence in the equation between distension and force ($\sigma = \kappa\epsilon + d$) is transformed into a proportional relationship ($\sigma = \kappa\epsilon$) which is possible by shifting the coordinates ($\sigma, \epsilon$) based upon the specific structure used.

In the present invention, this can be achieved by providing an appropriate prestress for the elastic ring or by an appropriate choice of the radius of the support cylinder. Both metallic rings and synthetic resins can have a linear region in their respective yield or distention curves. To achieve the requisite condition for the invention, it is also necessary to exclude any changes in axial force which can be accomplished by providing the axial ends of the reservoir as folds equivalent to the folds of a bellows.

Apart from operations utilizing a new geometric principle for ensuring a constant pressure dispensing of a liquid medicament, the system of the invention has other important advantages.

For example, it allows the integration of the reservoir and the elastic annular body in a single silicone rubber ring which can generate, upon being prestressed, the requisite force upon the liquid. Since a single body is used, it can be made very inexpensively and is reproducible by injection molding processes.

By providing inwardly directed axial folds at the opposite axial ends of the silicone rubber ring at the reservoir, axial forces which would create nonlinear conditions, can be rendered ineffective.

A special advantage for external application of the pump enables a separation between application part and pump part of the device.

This separation allows the pump to be assembled by insertion of the application part into the pump part in an especially simple way and also allows for a given pump structure selection using application parts having reduction cannulae of different lengths and passages of different cross sections and lengths, in general, so that the discharge rate in terms of volume per unit time can be varied with ease.

Bearing in mind that the insulin dependent patients may require between 10 and 100 insulin units per day, the possibility of easily selecting the pump rate by simply changing the application part, will be seen to be especially important.

All of the important parts of the apparatus including the silicone rubber body, the base of the housing together with the integrally molded support member thereon and the cover for the housing provided with the application part can all be injection molded from synthetic resin material highly economically so that the device can have a low cost.

To increase the life of the device, for example, with an implantable embodiment thereof, a toroidal metal spring, preferably a coil spring formed by joining opposite ends of a cylindrical coil spring, can be embedded in the silicone rubber ring.

Apart from silicone rubber, we may make use in an implantable embodiment of the invention any one of a number of biocompatible and bioresistive materials, e.g. titanium for the housing and polyurethane for the liquid reservoir. Instead of a cylindrical geometry, moreover, any other geometry can be used including a polygonal geometry of the support as long as the physical principles developed above continues to apply.

BRIEF DESCRIPTION OF THE DRAWING

The above objects, features and advantages of our invention will become more readily apparent from the following description, reference being made to the accompanying highly diagrammatic drawing in which.

SPECIFIC DESCRIPTION

Figure 1:
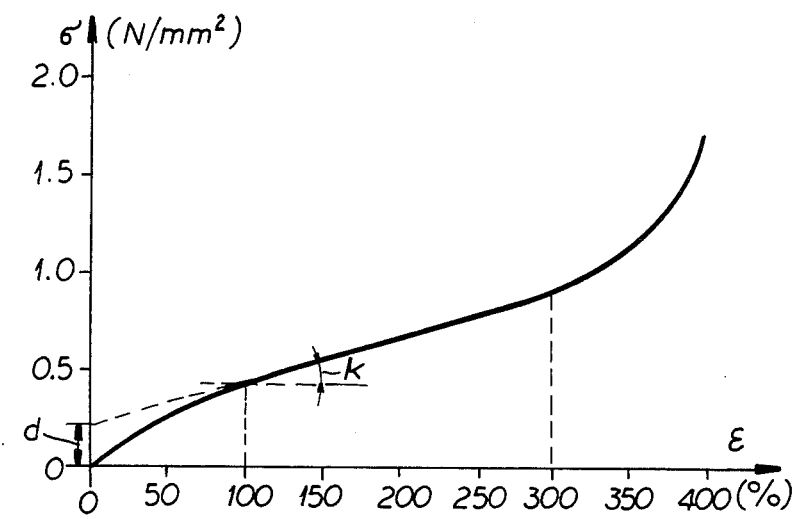
FIG. 1 is a graph showing the relationship between force in Newtons per square millimeter ($N/mm^2$) and elongation or distention ($\epsilon$) in percent of original length dimension, i.e. reservoir circumference in the present case, of the elastic material of the body used to compress the reservoir, i.e. silicone rubber.

The relationship between force ($N/mm^2$) and distention ($\mu$) of a silicone rubber synthetic resin is last seen in FIG. 1.

With maximum distention in the region of about 400%, the force/elongation relationship assumes a highly nonlinear relationship. For elongations of between 100% and 300%, however, the relationship is practically linear, i.e. a reduction in the distention gives rise to a practically linear reduction in the force which the resilient member generates.

Further relief of the stress on the elastic material results again in a nonlinear relationship as represented at the lower end of the graph shown in FIG. 1 and the prestress is selected so that practically all of the liquid is expelled from the reservoir before the elastic body is relaxed to a point below this linear range.

The slope of the linear portion is represented at k and its intersection with the Y-axis or ordinate is indicated at d as extrapolated in broken lines.

Figure 4:
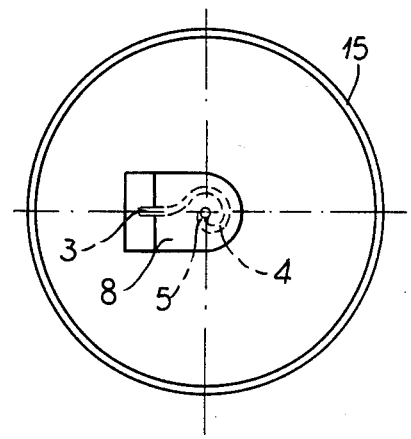
FIG. 4 is a bottom plan view of the cover.
Figure 5:
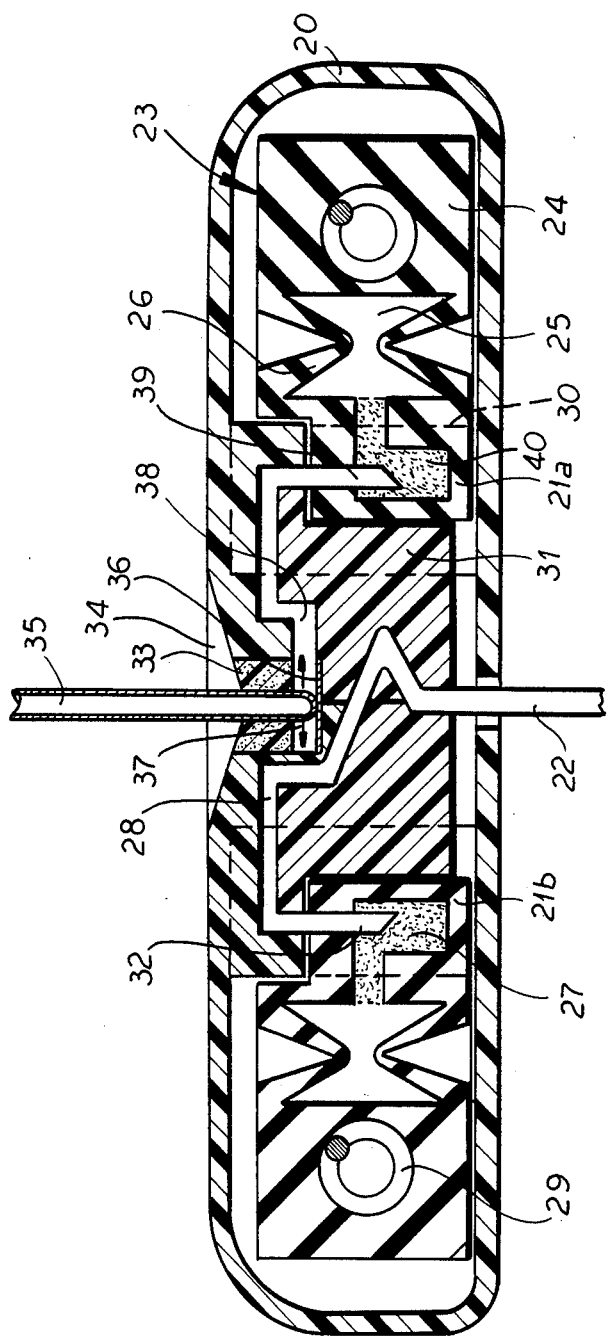
FIG. 5 is a cross-sectional view showing the relationship of an application part using a catheter for a modified device otherwise utilizing the principles described in connection with the device of FIGS. 2–4.

The elastic spring formed by the body 7 described below in connection with FIGS. 2–4 and even FIG. 5 is intended to operate in the linear range shown in FIG. 1.

Figure 3:
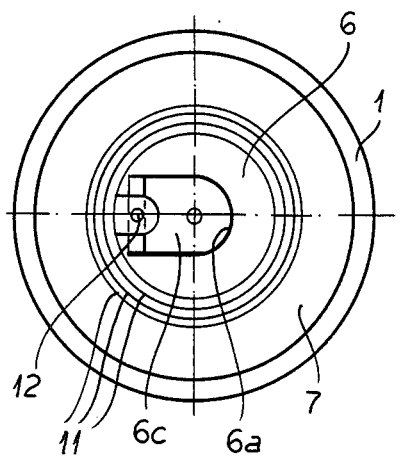
FIG. 3 is a plan view of the device shown in FIG. 2 with the cover removed.
Figure 2:
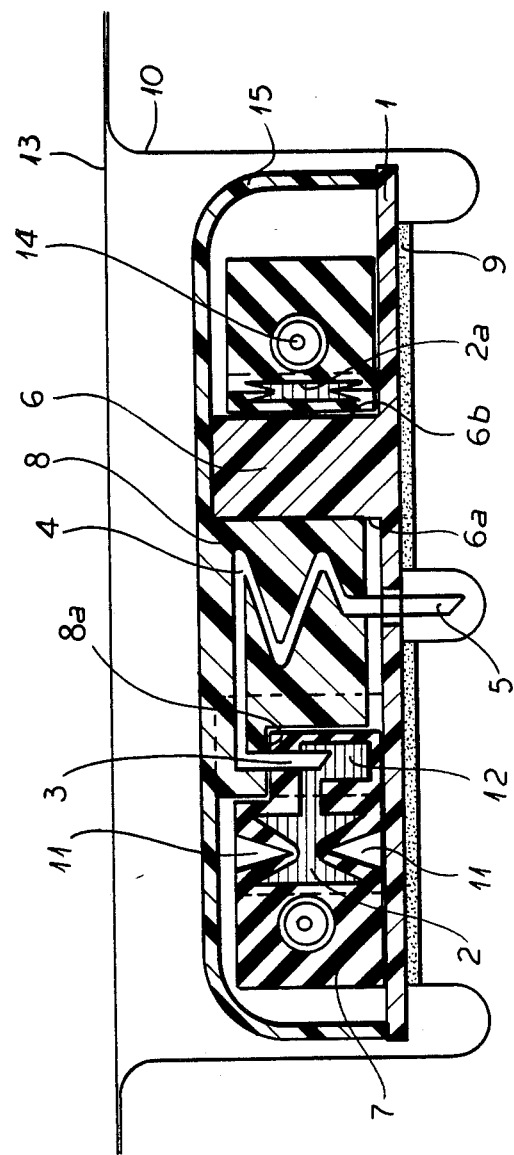
FIG. 2 is a cross-sectional view through the dispensing device of the present invention in which the foil thickness has been shown in single line form in order to preserve proportions because of the thinness of the foil.

The device of FIGS. 2–4 has been shown somewhat diagrammatically and thus at the left-hand side one can see the reservoir 2 in its full state whereas at the right-hand side of this FIGURE the reservoir is shown in its nearly empty state just before complete emptying. FIG. 2 also shows the device as it is packaged, i.e. before it is applied to the patient. In the course of application to the patient, the foils 10 and 13 forming the packaging area, of course, stripped from it.

The device for dispensing the liquid medicament shown in FIGS. 2–4 comprises a lower housing part or base 1 formed unitarily with a cylindrical support 6 which has inner and outer cylindrical walls 6a and 6b, the latter supporting the inner wall of a flexible reservoir 2 for a liquid medicament.

Surrounding the reservoir 2 and acting upon a rear wall 2a thereof is a radially elastically prestressed (expanded) annular body 7, whose prestress compresses a liquid medicament in reservoir 2 and generates the force required to discharge that medicament. The compressive force is taken-up by the support surface 6b.

As shown in the drawing, the reservoir 2 is preferably formed in a single piece at low cost by injection molding with the annular body 7 and out of a silicone rubber. To avoid application of axial forces to the liquid in the reservoir, the opposite axial ends of the reservoir 2 are formed with bellows-like inwardly directed folds 11.

A cover 15 of a rigid biologically compatible synthetic resin metal or titanium or another biologically compatible metal, is formed unitarily with an application part 8 which fits snugly in the cylindrical boss which forms the support 6 and is provided with a passage 4 whose length and cross section define the outflow rate from the reservoir. Since a variety of such application parts may be stocked, each with passages of different calibers and/or length, the particular pump assembly for use to suit the needs of a particular patient may be assembled by simply selecting one of these application parts and applying it to the standard base and reservoir assembly.

By way of a specific example, it should be noted that a typical dispenser of the type shown in FIGS. 2–4 can hold a dispensable volume of the medicament which is between 1 and 5 ml.

We have made extensive investigations into the diameters and lengths of the constructive passages 4 which should be used for dispensing various amounts of material over a given period of time and these results will, of course, vary depending upon the medicament used. For insulin in a glycerin vehicle, a length of the passage 4 of about 40 mm and an inner diameter of 0.02 mm can be used to deliver the contents of the reservoir of between 1 and 5 ml over a period of 25 to 30 hours. For a 60 micrometer ($\mu$) diameter of the passage 4 with a length of 20 mm with the body 7 and spring 14 dimensioned to yield a pressure of one bar for dispensing the liquid, we can achieve a flow a substantially 1 ml in 6.5 minutes with a substantially linear rate of approximately 0.15 ml per minute.

When the passage 4 is a tube which has an inner diameter of substantially 0.02 mm the outer diameter should be 0.2 mm, the same outer diameter being used when the tube has an inner diameter of about 60 mm.

The injection needle can project about 5 mm beyond the base and can have an outer diameter of 0.3 mm.

In practice, good results have been obtained with a unit in which the overall axial dimension of the dispensers is about 1.2 cm and the silicone rubber annular body/reservoir diameter is about 5 cm. Doubling these dimensions with a corresponding increase in the reservoir capacity can allow an implanted unit to operate for four weeks before refilling at a suitably reduced delivery rate. In all cases, however, the rate of delivery is substantially constant.

Rotation of the silicone rubber structure formed by the reservoir 2 and the body 7 is prevented on the base 1 by forming the assembly 2,7 with an inwardly projecting valve 12 which fits into an outwardly open cut-out 8c in the boss which forms the application part 8 and which fits into the correspondingly shaped seat 6c of the support 6. Thus the parts 6,8 and 2,7 are prevented from rotating with respect to one another.

The part 8 has an overhang 8a disposed above the valve and which carries a needle 3 adapted to penetrate the valve 12 (FIG. 2) to connect the passage 4 therewith.

The other end of the passage 4 is provided with an outlet cannula, preferably an injection needle 5, which is also shown in FIG. 2 to be covered with the foil 10 so that it is exposed when the foil 10 is stripped from the device. The application part 8 can be molded in one piece with the remainder of the cover 15, e.g. by injection molding.

For long term storage of the dispenser, it is packaged between a pair of foils 10 and 13, preferably aluminum foils.

To enable the dispenser to be applied to the body of the patient, a double-side adhesive foil 9 is provided, one adhesive side of this foil is applied directly to the base 1 while the other surface is masked by the metal foil 10. When the foil 10 is stripped from the adhesive of foil 9, the needle 5 is exposed and the device can be pressed against the surface of the body with the needle penetrating the skin for percutaneous administration.

In many cases, resiliency decays with age and to ensure long term potency of the dispenser, a metal spring 14 may be encased in the silicone rubber body 7.

The metal spring 14 consists of a coil spring whose ends have been connected together to form a torus.

When filling of the reservoir is required and the dispenser has been removed from its package the cover may be pulled out and the needle inserted directly in the valve 12. The liquid forced into the reservoir distends the reservoir by moving 2a outwardly and stretching the spring 14 and the annular body 7. The cover is then replaced and the dispenser fitted to the body as described, thereby percutaneously dispensing the liquid medicament over a prolonged period while the dispenser is retained on the body by the adhesive strip.

As can be seen from FIG. 5, when the infusion device is implanted in the body, the cover and base can be formed in one piece as shown at 20 and two valves 21a and 21b can be provided on the unitary body 23 which includes the annular resilient part 24 and the reservoir with its inward folds 26.

In this embodiment, however, a filter 27 can be provided in the valve 21b to function, together with the passage 28 which extends to the outlet cannula, to define the rate of outflow, simultaneously filtering any foreign material from the dispensed medicament before it enters the body. The housing 20 may be fused from several parts by thermal wedging after the device has been assembled.

As in the embodiment of FIGS. 2–4, the implantable dispenser of FIG. 5 has a coil spring 29 whose ends are joined together to form an endless toroidal spring supporting the elastic ring 24.

The reservoir is braced against a wall 30 formed on the housing and the valves 21a and 21b reach into notches in this support as previously described.

The housing is formed with an application part 31 carrying a needle 32 which penetrates into the valve 21b to discharge the liquid medicament in the manner which has been described with reference to the embodiment of FIGS. 2–4. It is also provided with a self-sealing valve plug 33 at the base of a depression 34 readily sensed through the skin by palpation when the device is implanted subcutaneously. Thus a refilling needle 35 can be inserted through the skin in the region of the depression as detected by palpation to refill the reservoir 25.

To this end, a metal plate 36 is provided to prevent excessive penetration of the needle 35 and lateral orifices 37 thereof discharge the medicament into a space 38 which is connected via a further needle 39 with the valve 21a. Thus when the device is assembled, both valves 21a and 21b are pierced by respective needles 32 and 39. Valve 21a is also filled with a filler material 40 as a further precaution against passage of foreign material on refilling into the reservoir.

In this embodiment, moreover, the outlet cannula is a catheter 22 rather than an injection needle.

Of course, from the foregoing description, it is possible to immediately recognize the important features of the invention.

Firstly, there is the unique geometry, apart from the ability to substitute application parts which permit selection of the discharge rates which ensures that there will be a constant pressure over the entire course of administration substantially to the end of the discharge and a complete discharge of a liquid medicament so that the discharge is at a constant rate.

Secondly, the infuion pump has an adhesive foil structure which is rendered effective by removal of the foil packaging to allow the infusion pump to be mounted on the body.

Thirdly, the dispenser has a uniquely integrated reservoir and prestressed ring in which the spring force is amplified by the metal spring to ensure long term effectiveness even after storage which might cause deterioration so that the distension of the body 7 or 24 can begin from its already prestressed state by the injection of the liquid medicament into the reservoir.

Fourthly, the reservoir has the bellows-like folds 11 which eliminate axial forces upon the liquid.

The passage 4 or 28 can be a bore or a thin metal tube or a passage formed by etching of metal layers by high precision lithographic processes and can be calibrated with or without a filter. The passage thus can be made with high precision at low cost.

The handling of the pump is also very simple and convenient, since the upper layer 13 of the relatively soft packaging foil can be removed, the pump filled, the application part replaced, the pump removed from the softer lower packaging foil 10, thereby exposing an adhesive surface of the foil 9, and the pump applied to the body in the manner described. The pump can have a size which can correspond to a modern EKG electrode and the adhesive itself can be a biocompatible adhesive well known to the art.

We claim:

1. A device for administering a liquid medicament to a patient at a substantially constant rate, said device comprising:
   a housing formed with a generally cylindrical support;
   a flexible collapsible annular reservoir containing said medicament and surrounding said support and braced thereagainst, said reservoir having an inwardly contractible wall which is distended when said reservoir is filled with said medicament;
   an annular resilient body surrounding said reservoir and in contact therewith in an unstressed state of said body, said body being distended upon filling of said reservoir with said medicament to apply an inward radial force to said wall for pressurizing said medicament in said reservoir; and
   a passage formed in said housing and connected to said reservoir while having an outlet adapted to communicate with an internal part of said patient, said passage having a cross section and length and structure controlling outflow of said medicament in relation to the annular force applied to said wall and the contraction of said wall under said force during discharge of said medicament that said discharge is effected with a substantially constant pressure over substantially the entire discharge period.

2. The device defined in claim 1 wherein said housing is formed with a base provided with said support, and a cover affixed to said base and enclosing said body and said reservoir.

3. The device defined in claim 2 wherein said cover is formed with said passage on a cylindrical boss which fits into said cylindrical support, said support being hollow to receive said boss.

4. The device defined in claim 3, further comprising a two-part metal foil package hermetically enclosing said housing for long-term storage of the device.

5. The device defined in claim 4 wherein said metal foil package is composed of aluminum foil.

6. The device defined in claim 4 wherein said base has an underside from which said outlet extends, said device further comprising a double-sided adhesive foil bonded to said underside and to metal foil of said package.

7. The device defined in claim 1 wherein said body and said reservoir are integrated in a unitary annular member.

8. The device defined in claim 7 wherein said member is composed of a silicone rubber.

9. The device defined in claim 7 wherein said body is provided with a radially prestressed cylindrical metal spring surrounding said reservoir to increase the long-term stability of the device.

10. The device defined in claim 9 wherein said spring is enclosed in said body.

11. The device defined in claim 9 wherein said spring is a coil spring having coil ends connected together and forming a toroid.

12. The device defined in claim 1 wherein said reservoir is provided between said wall and said support with bellows-like annular folds at opposite axial sides of said reservoir to eliminate any effect of axial forces on collapse of said reservoir.

13. The device defined in claim 12 wherein said folds extend into said reservoir.

14. The device defined in claim 1 wherein said support is annular, said device further comprising an application part inserted in said support and secured against rotation therein, said part being formed with said passage and said outlet and defining the rate at which said medicament is dispensed to said patient.

15. The device defined in claim 14 wherein said outlet is an injection needle.

16. The device defined in claim 14 wherein said housing comprises a lower member formed with said support and an upper member mounted on said lower member and provided with said application part.

17. The device defined in claim 1, further comprising a valve communicating with said reservoir for percutaneous refilling thereof by a needle injected into said valve.

18. The device defined in claim 1 wherein said passage is formed between said reservoir and said outlet with a filter at least in part controlling said rate.

19. The device defined in claim 1 wherein said outlet is a catheter.

* * * * *